(12) United States Patent  (10) Patent No.: US 9,095,276 B2
Carlson et al.  (45) Date of Patent: Aug. 4, 2015

(54) BREATH END-TIDAL GAS MONITOR

(75) Inventors: Lee R. Carlson, Pleasanton, CA (US); Edward A. McClatchie, Orinda, CA (US); Joe Martinosky, Wildwood, MO (US); Ralph Walden, Granite City, IL (US); Elvir Causevic, Denver, CO (US)

(73) Assignee: Capnia, Inc., Redwood City, CA (US)

( * ) Notice: Subject to any disclaimer, the term of this patent is extended or adjusted under 35 U.S.C. 154(b) by 1097 days.

(21) Appl. No.: 13/153,169

(22) Filed: Jun. 3, 2011

(65) Prior Publication Data

US 2012/0150055 A1  Jun. 14, 2012

Related U.S. Application Data

(62) Division of application No. 10/561,561, filed as application No. PCT/US03/19310 on Jun. 19, 2003, now Pat. No. 8,021,308.

(51) Int. Cl.
*A61B 5/08* (2006.01)
*A61B 5/083* (2006.01)
*A61B 5/087* (2006.01)

(52) U.S. Cl.
CPC . *A61B 5/083* (2013.01); *A61B 5/08* (2013.01); *A61B 5/087* (2013.01); *A61B 5/0833* (2013.01); *A61B 5/0836* (2013.01)

(58) Field of Classification Search
CPC ....... A61B 5/08; A61B 5/0833; A61B 5/0836
USPC ................................................. 600/532, 543
See application file for complete search history.

(56) References Cited

U.S. PATENT DOCUMENTS

| 3,858,573 | A | 1/1975 | Ryan et al. |
| 3,910,261 | A | 10/1975 | Ragsdale et al. |
| 4,423,739 | A | 1/1984 | Passaro et al. |
| 5,003,985 | A | 4/1991 | White et al. |
| 5,140,981 | A | 8/1992 | Lindstrom |
| 5,293,875 | A | 3/1994 | Stone |
| 5,445,161 | A | 8/1995 | Huang |
| 5,573,005 | A | 11/1996 | Ueda et al. |
| 6,099,481 | A | 8/2000 | Daniels et al. |
| 6,251,082 | B1 | 6/2001 | Rayburn |
| 6,544,190 | B1 | 4/2003 | Smits et al. |
| 6,582,376 | B2 | 6/2003 | Baghdassarian |

(Continued)

*Primary Examiner* — Michael D'Angelo
*Assistant Examiner* — Christian Jang
(74) *Attorney, Agent, or Firm* — Morrison & Foerster LLP

(57) ABSTRACT

An improved apparatus and method for capturing and analyzing the end-tidal portion of an exhalation. The $CO_2$ level of air drawn into the system (10) is monitored to distinguish inhalation and exhalation of breath. Upon detection of a decrease in the $CO_2$ level in the air drawn into the system (10), indicating a transition between exhalation and inhalation a pair of flow selector valves (26, 28) are operated to capture the end-tidal volume of air drawn into the system (10) immediately prior to the detection of the decrease in the $CO_2$ level. Incoming air is diverted around the captured volume of air, and the $CO_2$ levels are continually monitored to ensure that the captured volume of air corresponds to the end-tidal portion of an exhalation. Once the captured volume of air is positively identified as the end-tidal portion of an exhalation, the captured volume is routed through a gas analyzer (44) for analysis of one or more predetermined gas levels.

8 Claims, 4 Drawing Sheets

(56) References Cited

U.S. PATENT DOCUMENTS

| | | | |
|---|---|---|---|
| 6,733,463 | B2 | 5/2004 | Moilanen et al. |
| 8,021,308 | B2 | 9/2011 | Carlson et al. |
| 2005/0177056 | A1 | 8/2005 | Giron et al. |
| 2007/0232950 | A1 | 10/2007 | West |
| 2008/0119753 | A1 | 5/2008 | Ricciardelli et al. |
| 2008/0228096 | A1 | 9/2008 | Jaffe et al. |
| 2009/0118633 | A1 | 5/2009 | Jaffe et al. |

BREATH END-TIDAL GAS MONITOR

CROSS-REFERENCE TO RELATED APPLICATIONS

This application is a divisional of U.S. patent application Ser. No. 10/561,561, which has an International filing date of Jun. 19, 2003, and which is a National Phase application under 35U.S.C. §371 of International Application No. PCT/US2003/019310, filed on Jun. 19, 2003, each of which is hereby incorporated by reference in its entirety.

TECHNICAL FIELD

The present invention is related to gas analyzer systems, and in particular, to an improved gas analyzer system configured to obtain accurate gas analysis measurements of the a selected portion of a periodic gas pattern, such as the end-tidal portion of an exhalation from a test subject.

BACKGROUND ART

Often, there is the need to obtain measurements of the proportions and levels of gases present in a periodic or time-varying gas pattern, such as the breath of a patient. Analysis of the gases present in the breath of a patient is commonly utilized as a non-invasive procedure for obtaining a representation of the proportions and levels of gases in the patient's blood. It is known that air in the deep alveolar pockets of a patients lungs is composed of a mixture of gases which is in close equilibrium with the mixture of gases present in the patient's blood. During a patient's breath cycle, the last portion of an exhalation, i.e. the "end-tidal" portion is believed to provide the most accurate representation of the mixture of gases in the deep alveolar pockets of the lungs.

Conventional breath analyzer devices obtain a number of measurements of gas concentrations in a patient's breath over a predetermined period of time. These measurements are utilized in a mathematical curve-fitting analysis which subsequently provides an approximate measurement of the gas concentrations for discrete portions of the patients breath, including the end-tidal portion.

Accordingly, it would be advantageous to provide a system and method for analyzing the proportions and levels of one or more gases present in the breath of a patient, and which is capable of selectively analyzing only the end-tidal portion of the breath of a patient to provide an accurate direct measurement of the mixture of gases present in the patient's blood.

SUMMARY OF THE INVENTION

Briefly stated, the present invention is configured to acquire a selected sample of a time-varying or periodic gas pattern. A gas intake is routed to a detector configured to continually monitor the time-varying or periodic element of the gas pattern. Output gas from the detector is directed to a branch. The branch configured to direct the flow of gas either into a sample volume contained between first and second flow selector valves, or to bypass the sample volume and directly enter a third flow selector valve. An air pump is operatively coupled to the third flow selector valve to draw gas through the system from the gas intake, and to force the gas through a fourth flow selector valve where it is either exhausted from the system or redirected back to the sample volume. A gas output from the first flow selector valve is configured to exhaust air from the sample volume through one or more gas analyzer.

In an alternate embodiment, the present invention is configured to acquire a sample of exhaled air from an end-tidal portion of a patient's exhalation. A pair of air intakes are routed to a first flow selector valve. One of the pair of air intakes is configured to receive an exhalation from a patient or test subject, and preferably consists of a cannula adapted for tracheal or nasal insertion. The second air intake is configured to receive a supply of ambient air for diagnostic and calibration purposes. The second air intake preferably includes a $CO_2$ scrubber adapted to reduce the level of $CO_2$ present in the ambient air as it is drawn there through. Air output from the first flow selector valve is routed to a capnograph configured to continually monitor the level of $CO_2$ present. Output air from the capnograph is directed to the input of a second flow selector valve. The second flow selector valve is configured to direct the flow of air either into a sample volume contained between third and fourth flow selector valves, or to bypass the sealable sample volume and directly enter the fourth flow selector valve. An air pump is operatively coupled to the fourth flow selector valve to draw air through the system from either of the pair of air intakes, and to force the air through a fifth flow selector valve where it is either exhausted from the system or redirected back to the sealable sample volume. An air output from the third flow selector valve is configured to exhaust air from the sample volume through a gas analyzer.

A method of the present invention for capturing and analyzing a select portion of an periodic or time-varying gas patterns involves monitoring the periodic element of gas drawn into the system. Upon detection of a level of the periodic element in the gas drawn into the system reaching a predetermined threshold, a flow selector valve is operated to isolate a volume of air drawn into the system immediately prior to the detection of the threshold level. Incoming gas is diverted around the captured volume of gas, and the periodic element threshold levels are continually monitored to ensure that the captured volume of gas corresponds to the desired portion of the periodic or time-varying gas pattern. Once the captured volume of gas is positively identified as the desired portion, the captured volume is routed through one or more gas analyzers for analysis of one or more predetermined gas levels.

An alternate method of the present invention for capturing and analyzing the end-tidal portion of an exhalation involves monitoring the $CO_2$ level of air drawn into the system As the monitored $CO_2$ level increases, it is known that the patient is exhaling. Upon detection of a decrease in the $CO_2$ level in the air drawn into the system, a pair of flow selector valves are operated to capture the volume of air drawn into the system immediately prior to the detection of the decrease in the $CO_2$ level. Incoming air is diverted around the captured volume of air, and the $CO_2$ levels are continually monitored to ensure that the captured volume of air corresponds to the end-tidal portion of an exhalation. Once the captured volume of air is positively identified as the end-tidal portion of an exhalation, the captured volume is routed through one or more gas analyzers for analysis of one or more predetermined gas levels.

The foregoing and other objects, features, and advantages of the invention as well as presently preferred embodiments thereof will become more apparent from the reading of the following description in connection with the accompanying drawings.

DESCRIPTION OF DRAWINGS

In the accompanying drawings which form part of the specification:

FIG. 2 is a simplified component diagram of a breath analyzer of the present invention, with flow selector valves configured for breath pass-through;

Corresponding reference numerals indicate corresponding parts throughout the several figures of the drawings.

BEST MODE FOR CARRYING OUT THE INVENTION

The following detailed description illustrates the invention by way of example and not by way of limitation. The description clearly enables one skilled in the art to make and use the invention, describes several embodiments, adaptations, variations, alternatives, and uses of the invention, including what is presently believed to be the best mode of carrying out the invention.

Figure 1:
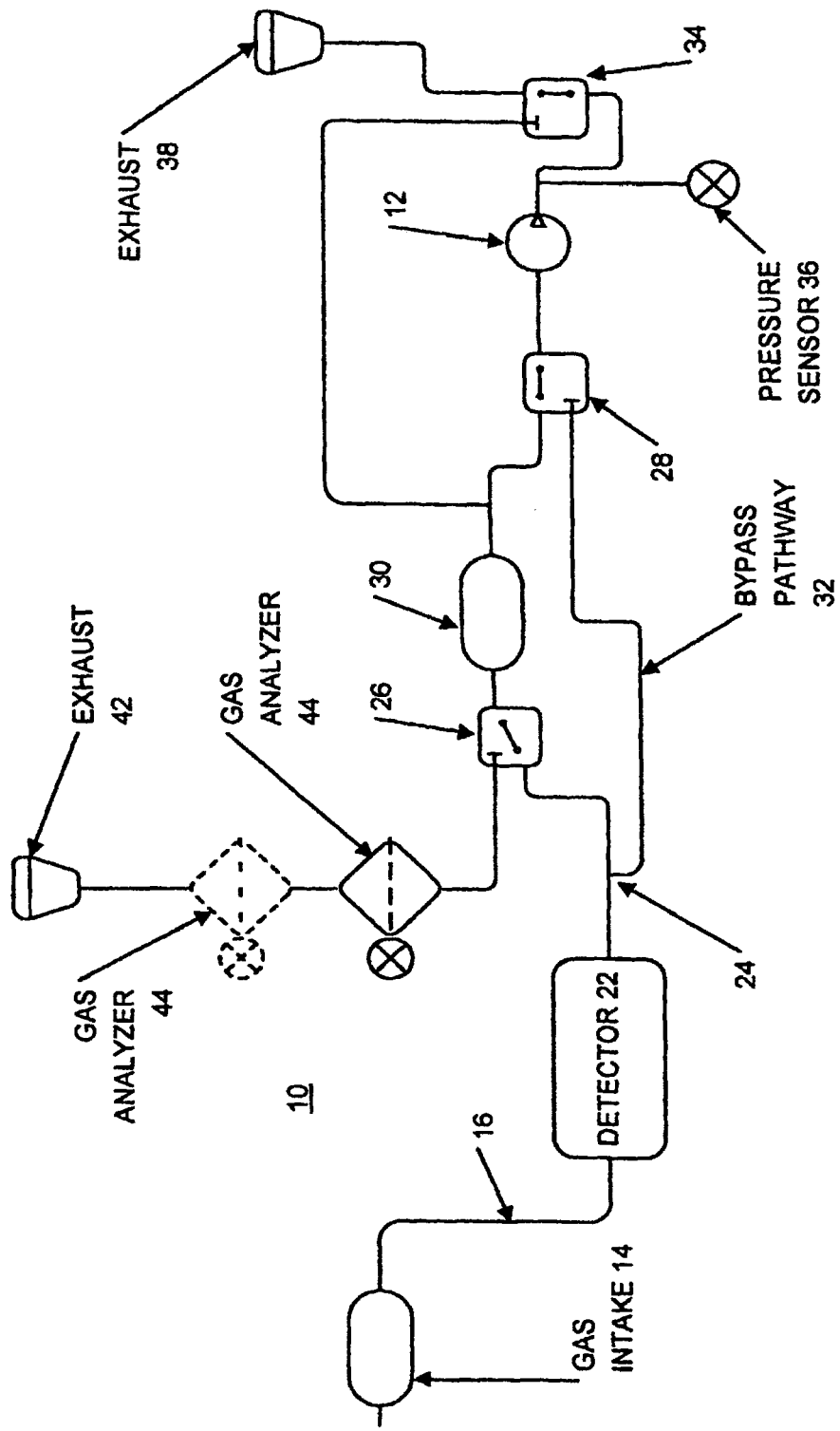
FIG. 1 is a simplified component diagram of the periodic gas analyzer of the present invention.

Turning to FIG. 1, a time-varying or periodic gas analyzer of the present invention is shown generally at 10. A pump 12 is operated to draw air into the apparatus 10 through a gas intake 14 operatively placed to receive gas from a time-varying or periodic gas pattern. Interconnecting tubing 16 routes the received gas to a detector 22. The detector 22 is further configured to continually monitor the level of a periodic gas element or component present in the input airflow, and to provide one or more associated output signals representative of the level reaching a predetermined threshold. These associated output signals may include, but are not limited to, a measure of the periodic gas element or component present in the input airflow, an indication of an increase in the measure of the periodic gas element or component present in the input airflow, or an indication of a decrease in the measure of the periodic gas element or component present in the input airflow.

Downstream from the detector 22, a "T" branch 24 and a series of flow selector valves 26 and 28 and associated interconnecting tubing define a sample volume 30 disposed between flow selector valves 26 and 28, and a bypass pathway 32 disposed between the "T" branch 24 and the flow selector valve 28. The "T" branch 24 is configured to receive an output airflow from the detector 22 and to direct the output airflow through flow selector valve 26 into the sample volume 30, or into the bypass pathway 32 to flow selector valve 28.

Airflow exiting flow selector valve 28 is drawn through the pump 12 and routed to a flow selector valve 34. A pressure sensor 36 is operatively coupled to the air pathway between the pump 12 and the flow selector valve 34. Pressure sensor 36 is configured to monitor the air flow pressure level between the pump 12 and the flow selector valve 34, and to provide a warning in the event the monitored pressure level falls outside a predetermined range. Flow selector valve 34 is configured to selectively direct an output airflow to either an exhaust port 38, or to the sample volume 30. Flow selector valve 26 is configured to selectively isolate the sample volume 30 from the input airflow received from the "T" branch 24, and to selectively couple the sample volume 30 to an exhaust port 42 through at least one gas analyzer 44.

Those of ordinary skill in the art will recognize that a suitably configured control circuit, such as a logic circuit, a microprocessor, or a general purpose computer (not shown) may be used to control the individual flow selector valves 26, 28, and 34, responsive to the output of the detector 22. Furthermore the control circuit may be operatively coupled to the at least one gas analyzer 44 to provide an operator with one or more output representation of the gas analysis results and operation of the apparatus 10. Programming of a suitable control circuit to operate the above described components and to carry out the method of the present invention is considered to be routine to those of ordinary skill in the art of computer programming, and is not addressed further herein.

A method of the present invention for capturing and analyzing a select portion of a time-varying or periodic gas pattern involves monitoring the level of a periodic element or gas component in gas drawn into the apparatus 10 through the gas intake 14. The level of the periodic element or gas component is monitored using the detector 22, and is drawn in through the gas intake 14 and detector 22 by the pump 12. The airflow passes through the "T" branch 24, and into the sample volume 30 contained between flow selector valves 26 and 28. As the airflow exits the sample volume 30 through flow selector valve 28, it is drawn through the pump 12 and propelled through flow selector valve 34 to exit the apparatus 10 through the exhaust port 38.

As the monitored level of the periodic element or gas component in the incoming airflow through the gas intake 14 and detector 22 reaches a predetermined threshold, flow selector valves 26 and 28 are closed to capture, in the sample volume 30, the volume of air which was drawn into the apparatus 10 immediately prior to the detection of the threshold level by the detector 22.

Subsequent incoming gas flow drawn into the apparatus 10 by the pump 12 is diverted through the bypass pathway 32 at the "T" branch 24. The bypass pathway 32 is routed around the sample volume 30, permitting a continued draw of gas through the apparatus 10. The threshold levels of the continued draw of gas through the apparatus 10 are monitored by the detector 22 to ensure that the gas isolated within the sample volume 30 corresponds to the desired portion of an gas pattern, i.e. that the threshold levels of the gas drawn into the apparatus 10 satisfy a predetermined set of criteria, for example, that they are maintained for a predetermined period of time. Once the isolated gas in the sample volume 30 is positively identified as the desired portion, the captured volume is exhausted from the apparatus 10 through one or more gas analyzers 44 for analysis of one or more predetermined gas levels.

To drive the captured volume of air contained within the sample volume 30 through the one or more gas analyzers, the flow selector valve 34 is operated to divert the incoming air flow from the exhaust port 38 and instead, route the incoming gas flow into the sample volume 30. Simultaneously, the flow selector valve 26 is operated to open a pathway for gas flow to exhaust port 42 through the one or more gas analyzers 44.

With pump 12 operating at a known capacity, the flow rate of the incoming gas flow passing into the sample volume 30 is known. Accordingly, the flow rate of the volume of gas past the one or more gas analyzers 44 is known. Each gas analyzers 44 is selectively operated to sample the gas flow only for that portion of the gas flow which corresponds to the volume originally captured in the sample volume 30 which corresponds to the desired portion of the gas pattern.

Figure 2:
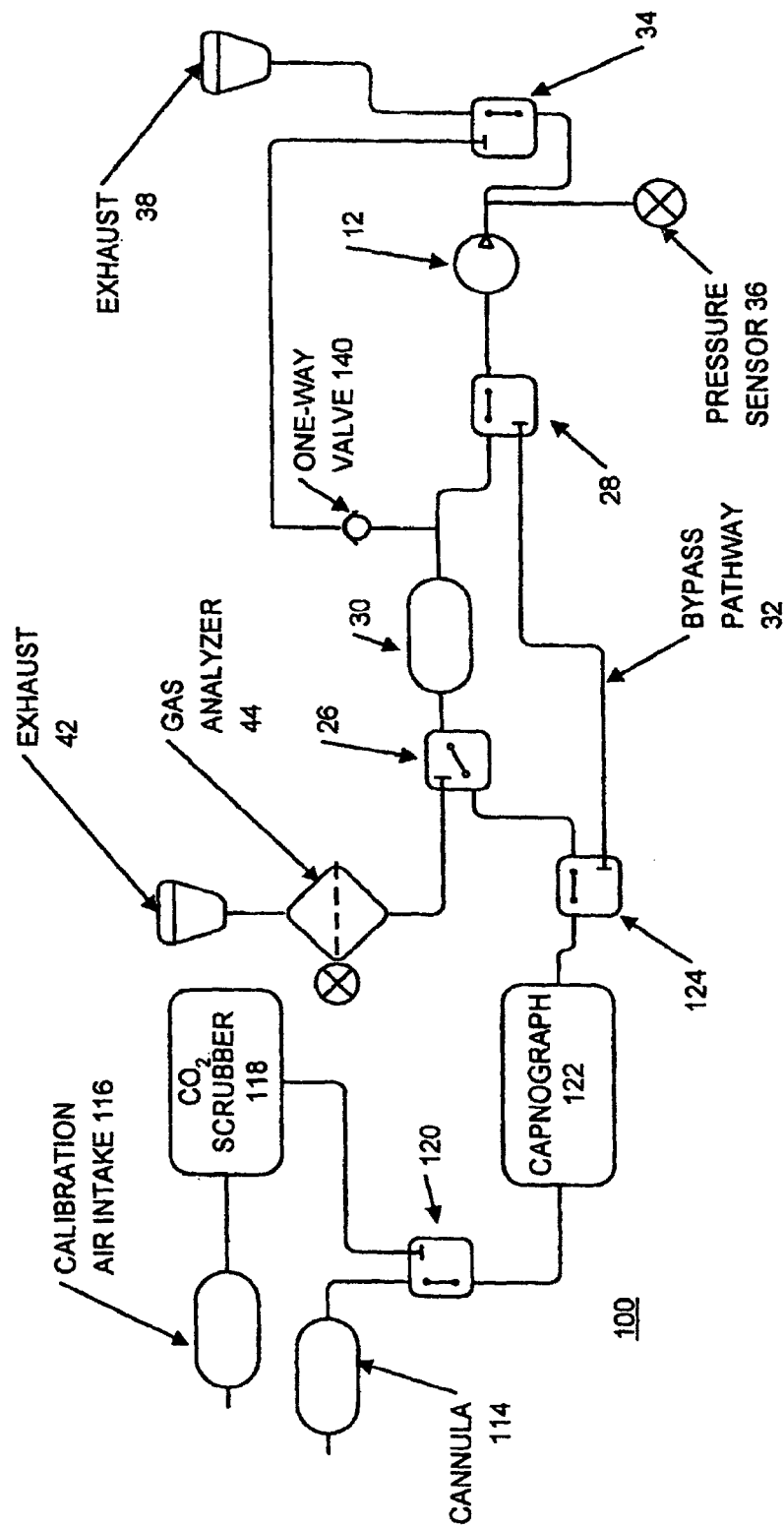

Turning to FIG. 2, a modification of the basic apparatus 10 shown in FIG. 1, particularly adapted for collecting and analyzing end tidal breath exhalations is shown generally at 100. Components which are unchanged in function from the embodiment shown in FIG. 1 have the same reference numerals as shown in FIG. 1. A pump 12 is operated to draw air into the apparatus 10 through either a cannula 114 operatively placed to receive air from a patient's lungs, or a calibration air intake 116. The calibration air intake 116 is operatively placed to receive ambient air, and includes a $CO_2$ scrubber 118 configured to reduce the level of $CO_2$ in the ambient air drawn through the calibration air intake 116. A flow selector valve 120 is configured to receive airflow from both the cannula 114 and the calibration air intake 116, and to select either the cannula 114 or the calibration air intake 116 to provide an input airflow to the apparatus 100.

Operatively coupled to the output of the flow selector valve 120 via interconnecting tubing, a capnograph 122 is configured to receive the input airflow to the apparatus 100. The capnograph 122 is further configured to continually monitor the level of $CO_2$ present in the input airflow, and to provide one or more associated output signals. These associated output signals may include, but are not limited to, a measure of the $CO_2$ present in the input airflow, an indication of an increase in the measure of the $CO_2$ present in the input airflow, or an indication of a decrease in the measure of the $CO_2$ present in the input airflow.

To calibrate the capnograph 122, the flow selector valve 120 is configured to draw ambient room air into the apparatus 100 through the calibration air intake 16 and past the $CO_2$ scrubber 118. In the $CO_2$ scrubber 118, the amount of $CO_2$ present in the drawn in ambient room air is reduced to a predetermined level, which is subsequently measured by the capnograph 122. Any discrepancy between the capnograph 122 $CO_2$ measurement and the predetermined level is an indication that the apparatus 100 may require calibration.

Downstream from the capnograph 122, a flow selector valve 124 optionally replaces "T" branch 24, to provide, with flow selector valves 26 and 28 and associated interconnecting tubing, a sample volume 30 disposed between flow selector valves 26 and 28, and a bypass pathway 32 disposed between flow selector valves 124 and 28. Flow selector valve 124 is configured to receive an output airflow from the capnograph 122 and to selectively direct the output airflow either through flow selector valve 26 into the sample volume 30, or into the bypass pathway 32 to flow selector valve 28.

Airflow exiting flow selector valve 28 is drawn through the pump 12 and routed to a flow selector valve 34. A pressure sensor 36 is operatively coupled to the air pathway between the pump 12 and the flow selector valve 34. Pressure sensor 36 is configured to monitor the air flow pressure level between the pump 12 and the flow selector valve 34, and to provide a warning in the event the monitored pressure level falls outside a predetermined range.

Flow selector valve 34 is configured to selectively direct an output airflow to either an exhaust port 38, or to the sample volume 30 through an optional one-way valve 140. One-way valve 140 is operatively disposed in the sample volume 30 adjacent the flow selector valve 28, such that an airflow entering the sample volume 30 through the one-way valve 140 will flow in the opposite direction to an airflow entering the sample volume through the flow selector valve 26.

Flow selector valve 26 is configured to selectively isolate the sample volume 30 from the input airflow received from the flow selector valve 124, and to selectively couple the sample volume 30 to an exhaust port 42 through at least one gas analyzer 44. Preferably, the at least one gas analyzer 44 includes a CO sensor configured to measure the level of CO in the airflow passing there through. In an alternative embodiment, the at least one gas analyzer 44 includes an $O_2$ sensor configured to measure the level of $O_2$ in the airflow passing there through.

Those of ordinary skill in the art will recognize that a suitably configured control circuit, such as a logic circuit, a microprocessor, or a general purpose computer (not shown) may be used to control the individual flow selector valves 120, 124, 26, 28, and 34, responsive to the output of the capnograph 122. Furthermore the control circuit may be operatively coupled to the at least one gas analyzer 44 to provide an operator with one or more output representation of the breath gas analysis results and operation of the apparatus 100. Programming of a suitable control circuit to operate the above described components and to carry out the method of the present invention is considered to be routine to those of ordinary skill in the art of computer programming, and is not addressed further herein.

A method of the present invention for capturing and analyzing the end-tidal portion of an exhalation involves monitoring the $CO_2$ level of aspirated breath air drawn from a patient's respiratory system into the apparatus 100 through the cannula 114. The $CO_2$ level of the incoming air is monitored using the capnograph 122. Normal breath airflow through the apparatus 100 is drawn in through the cannula 114 and capnograph 122 by the pump 12. The airflow passes through the flow selector valve 124, and into the sample volume 30 contained between flow selector valves 26 and 28. As the airflow exits the sample volume 30 through flow selector valve 28, it is drawn through the pump 12 and propelled through flow selector valve 34 to exit the apparatus 100 through the exhaust port 38.

Figure 3:
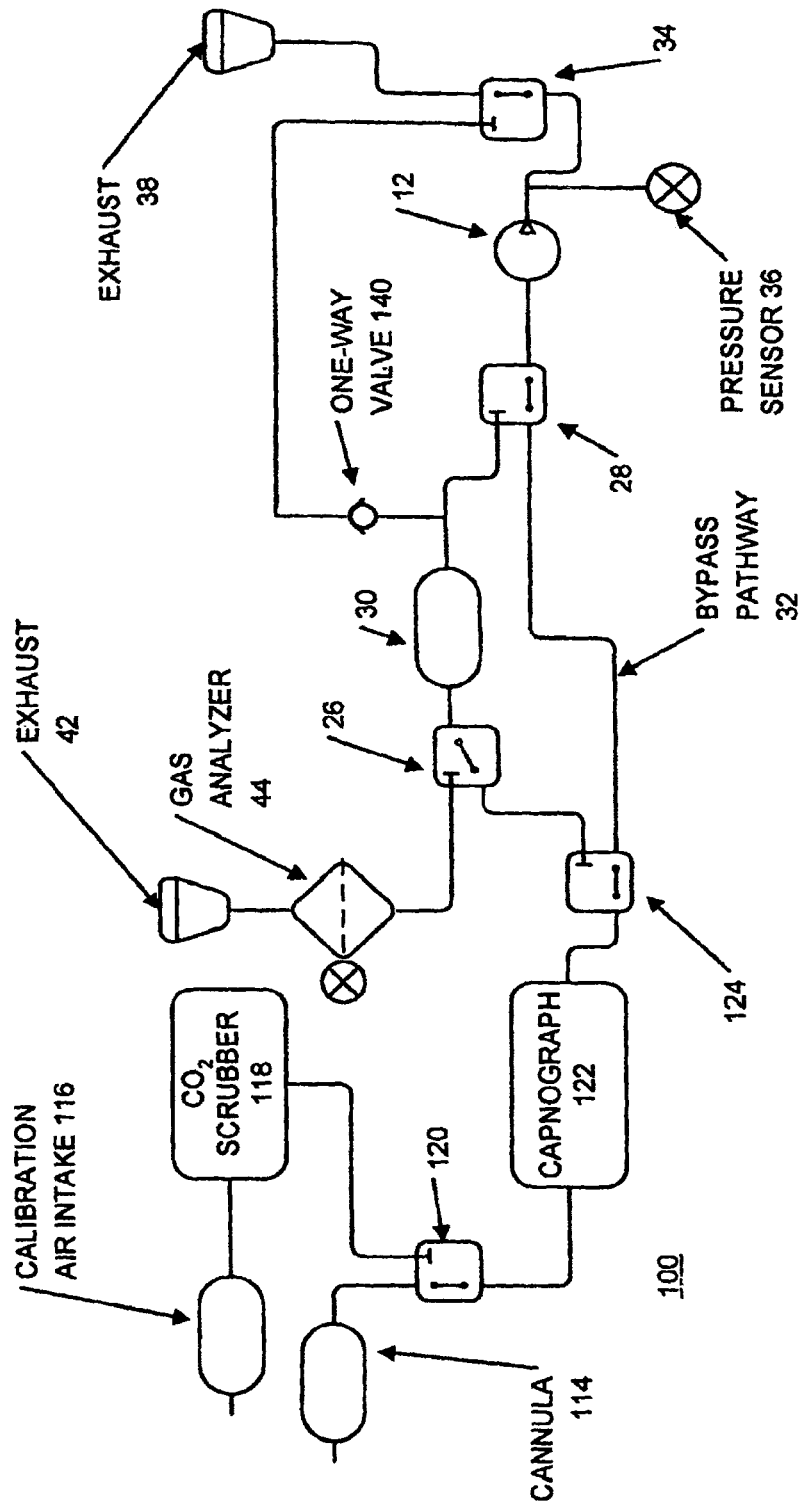
FIG. 3 is the breath analyzer of FIG. 2, with the flow selector valves configured for breath sample isolation.
Figure 4:
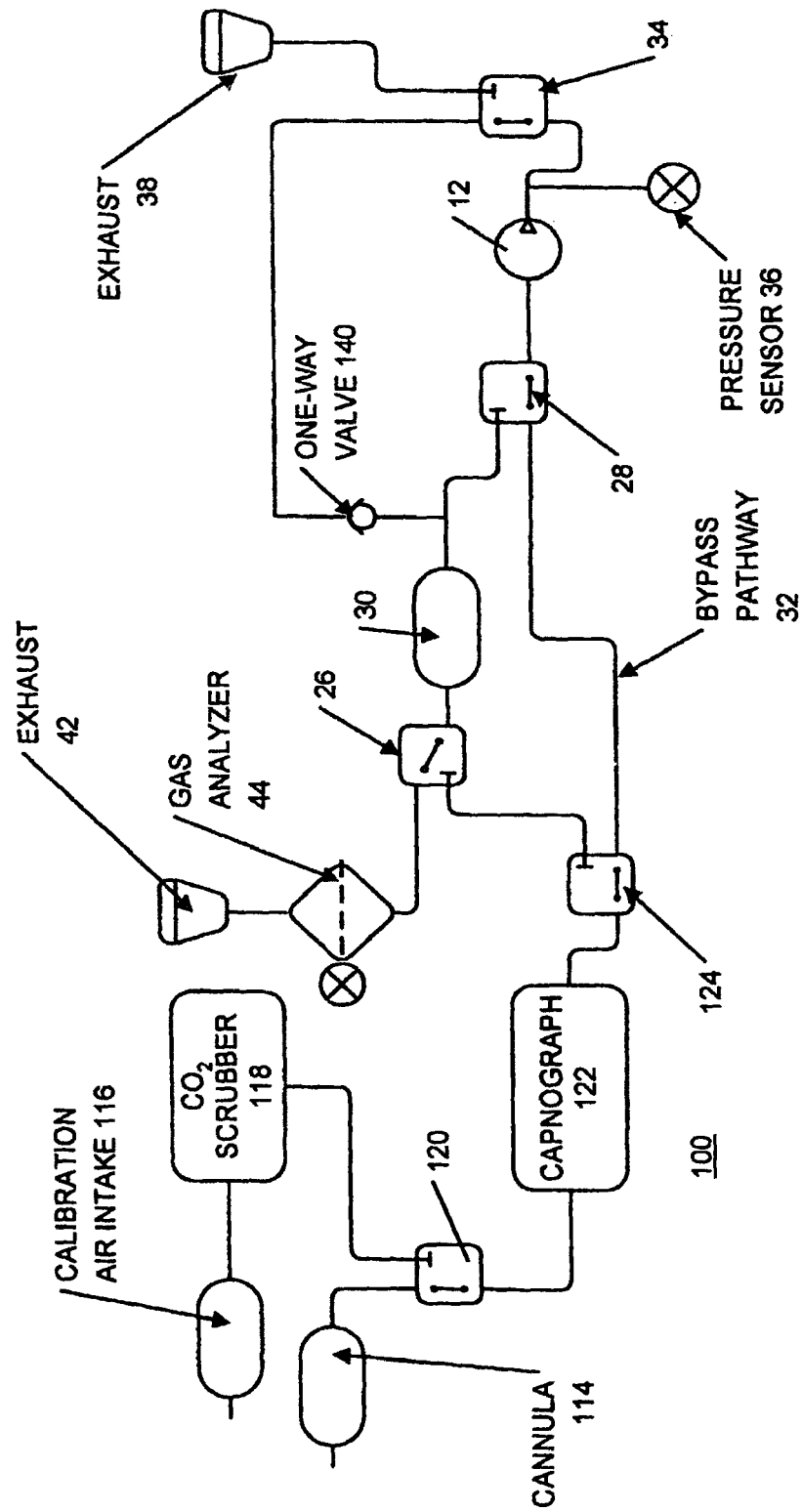
FIG. 4 is the breath analyzer of FIG. 2, with the flow selector valves configured for breath sample analysis.

As the monitored $CO_2$ level in the incoming airflow through the cannula 114 and capnograph 122 increases, it is known that the patient is exhaling. Upon detection by the capnograph 122 of a decrease in the $CO_2$ level of the air drawn into the apparatus 100 through the cannula 114, a flow selector valves 26 and 28 are closed, as shown in FIG. 3, to capture, in the sample volume 30, the volume of air which was drawn into the apparatus 100 immediately prior to the detection of the decrease in the $CO_2$ level by the capnograph 122.

Subsequent incoming air flow drawn into the apparatus 100 by the pump 12 is diverted through the bypass pathway 32 by the flow selector valve 124. The bypass pathway 32 is routed around the sample volume 30, permitting a continued draw of air through the apparatus 100. The $CO_2$ levels of the continued draw of air through the apparatus 100 are monitored by the capnograph 122 to ensure that the air isolated within the sample volume 30 corresponds to the end-tidal portion of an exhalation, i.e. that the $CO_2$ levels of the air drawn into the apparatus 100 continue to decrease for a predetermined period of time at a predetermined rate of decrease. Once the isolated air in the sample volume 30 is positively identified as the end-tidal portion of an exhalation, the captured volume is exhausted from the apparatus 100 through one or more gas analyzers for analysis of one or more predetermined gas levels.

To drive the captured volume of air contained within the sample volume 30 through the one or more gas analyzers, the flow selector valve 34 is operated to divert the incoming air flow from the exhaust port 38 and instead, route the incoming air flow into the sample volume 30 through the optional one-way valve 140. Simultaneously, the flow selector valve 26 is operated to open a pathway for airflow to exhaust port 42 through the one or more gas analyzers 44. The operative position of the one-way valve 140 in relation to the flow selector valve 26 causes the incoming air flow from the one-way valve 140 to drive the volume of air contained within the sample volume 30 through the flow selector valve 26 and through the one or more gas analyzers 44.

With pump 12 operating at a known capacity, the flow rate of the incoming air flow passing through one-way valve 140 into the sample volume 30 is known. Accordingly, the flow rate of the volume of air past the one or more gas analyzers 44 is known. Each gas analyzers 44 is selectively operated to sample the air flow only for that portion of the air flow which corresponds to the volume originally captured in the sample volume 30 which corresponds to the end-tidal portion of a patient's breath. Preferably, at least one gas analyzer 44 measures a level of CO present in the air flow passing there through. Alternatively, a gas analyzer measures a level of $O_2$ present in the air flow.

The present invention can be embodied in-part the form of computer-implemented processes and apparatuses for practicing those processes. The present invention can also be embodied in the form of computer program code containing instructions embodied in-part in tangible media, such as floppy diskettes, CD-ROMs, hard drives, or an other computer readable storage medium, wherein, when the computer program code is loaded into, and executed by, an electronic device such as a computer, micro-processor or logic circuit, the device becomes an apparatus for practicing the invention.

The present invention can also be embodied in-part the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented in a general-purpose microprocessor, the computer program code segments configure the microprocessor to create specific logic circuits.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

The invention claimed is:

1. A breath gas analyzer having a pump configured to draw a flow of air through a capnograph adapted to identify a transition point between an exhalation and an inhalation, and to subsequently direct said flow of air through at least one gas analyzer, comprising: a first flow selector valve disposed downstream from said capnograph, said first flow selector valve configured to selectively divert said flow of air into a sample volume or into a bypass pathway for routing around said sample volume; a second flow selector valve disposed downstream from said first flow selector valve, said second flow selector valve configured to isolate said sample volume from said first flow selector valve; a third flow selector valve disposed downstream from said second flow selector valve, said third flow selector valve configured to receive said flow of air from said bypass pathway and to isolate said sample volume from said pump; a fourth flow selector valve disposed downstream from said pump, said fourth flow selector valve configured to selectively exhaust said flow of air or to route said flow of air into said sample volume; and wherein said second flow selector valve is further configured to selectively exhaust said sample volume through the at least one gas analyzer.

2. The breath gas analyzer of claim 1 wherein said second flow selector valve and said third flow selector valve are responsive to signals from said capnograph to isolate said sample volume from said first flow selector valve and from said pump.

3. The breath gas analyzer of claim 1 wherein said fourth flow selector valve is responsive to signals from said capnograph to route said flow of air into said sample volume.

4. The breath gas analyzer of claim 3 wherein said fourth flow selector valve is responsive to signals from said capnograph to route said flow of air through a one-way valve into said sample volume.

5. The breath gas analyzer of claim 1 wherein said second flow selector valve is responsive to signals from said capnograph to exhaust said sample volume through the at least one gas analyzer.

6. The breath gas analyzer of claim 1 wherein the at least one gas analyzer includes a CO gas analyzer.

7. The breath gas analyzer of claim 1 wherein the at least one gas analyzer includes an $O_2$ gas analyzer.

8. The breath gas analyzer of claim 1 further including a microprocessor configured to receive signals from said capnograph and to control operation of each of said flow selector valves.

* * * * *